(12) United States Patent
Lindegren

(10) Patent No.: US 6,615,483 B2
(45) Date of Patent: Sep. 9, 2003

(54) METHOD FOR COATING A TIP REGION OF A MULTIPOLAR ELECTRODE LEAD

(75) Inventor: Ulf Lindegren, Stockholm (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/954,120

(22) Filed: Sep. 17, 2001

(65) Prior Publication Data

US 2002/0032963 A1 Mar. 21, 2002

(30) Foreign Application Priority Data

Sep. 18, 2000 (SE) .............................................. 0003341

(51) Int. Cl.[7] .............................................. H01B 43/00
(52) U.S. Cl. ................ 29/825; 427/2.24; 427/255.391; 600/374; 607/122; 607/123
(58) Field of Search ............................. 29/825; 607/122, 607/123; 600/374; 427/2.24, 255.391

(56) References Cited

U.S. PATENT DOCUMENTS

| | | |
|---|---|---|
| 4,784,160 A | 11/1988 | Szilagyi |
| 5,306,292 A | 4/1994 | Lindegren |
| 5,445,859 A * | 8/1995 | Lindegren et al. |
| 5,487,758 A * | 1/1996 | Hoegnelid et al. |
| 5,935,158 A | 8/1999 | Holmström et al. |
| 6,512,940 B1 * | 1/2003 | Brabec et al. |

FOREIGN PATENT DOCUMENTS

EP 0 043 461 1/1982

* cited by examiner

Primary Examiner—Carl J. Arbes
(74) Attorney, Agent, or Firm—Schiff Hardin & Waite

(57) ABSTRACT

In am method for coating a tip region of an multipolar electrode head adapted to be mounted at a distal end of a lead used preferably for providing heart stimulation by means of a heart stimulation apparatus, an electrode head is provided having a tip with a ceramic part in which a number of small spaced-apart conductive electrode surfaces are disposed, a region of the electrode head tip is directly coated with a tissue compatible material, such as TiN, so that all conductive electrode surfaces are coated in a single step coating operation without any masking operation.

7 Claims, 1 Drawing Sheet

METHOD FOR COATING A TIP REGION OF A MULTIPOLAR ELECTRODE LEAD

FIELD OF THE INVENTION

The present invention relates to a method for coating a tip region of a multipolar electrode head, of the type adapted to be mounted at a distal end of an electrode lead (pacing lead) used preferably for providing intracardial stimulation of heart tissue, and/or for sensing heart signals, by means of a heart stimulation apparatus or pulse generator.

DESCRIPTION OF THE PRIOR ART

A heart stimulation apparatus having an electrode device with a multipolar electrode head is disclosed in U.S. Pat. No. 5,306,292. This electrode head is a hemispherical electrode head fitted with a number (e.g. four) of round, closely spaced conductive surfaces that are uniformly distributed on the electrode head. The conductive surfaces are separated y an electrically insulating material, normally a ceramic material such as aluminum. The conductive surfaces are normally coated with a porous layer, such as titanium nitride (TiN) intended to enlarge the active surface of each conductive surface. At present the belief is that the conductive surfaces should be coated utilizing masking operations to avoid the coating material being deposited on the insulating material, to ensure that each conductive surface is in electrical contact only with tissue/body liquid and the conductor in the lead.

SUMMARY OF THE INVENTION

An object of the present invention is to devise a simplified method of manufacturing multipolar electrode heads with a porous layer.

The above object is achieved in accordance with the present invention in a method for coating a tip region of a multipolar electrode head, adapted to be mounted at a distal end of a lead preferably used for providing heart stimulation by connection to a heart stimulation apparatus, wherein an electrode head is provided having a tip with a ceramic part in which a number of small, spaced-apart conductive electrode surfaces are disposed, and wherein a region of the electrode head tip is directly coated with a tissue compatible material, so that all conductive electrode surfaces are coated in a single step coating operation without any masking operation.

The method consequently excludes the masking operation hitherto thought necessary. To be able to dispense with a masking operation greatly simplifies the manufacture of this type of electrode.

The invention is based on the surprising insight that it is possible to allow the porous layer to extend wholly or partly over the insulating material between the conducting surfaces, the dimensions, i.e. the effective conductive cross-section, of the porous layer being such that the electrical conduction through the tissue/body fluid between the conductive surfaces is not affected, this being due to the thinness of the layer as well as being due to the porosity of the material in the layer.

As a suitable coating material is preferably a porous material, the resistivity of which is at least equal to, but preferably higher than, the resistivity of cardiac body fluids. The thinness and porosity, i.e. the effective conductive cross-section, of the layers as well as the distance between the electrode surfaces are taken into account for determining the resistivity. Materials suitable for the coating step are preferably titanium nitride, carbon and platinum black.

The above object is also achieved in accordance with the principles of the present invention in a method for manufacturing a multipolar electrode head by providing a non-conductive part, such as a ceramic part, with a number of recesses or notches therein, inserting respective conductive wires into the recesses or notches to form a number of spaced-apart electrodes, separated by the non-conductive material, and directly coating the surface of the non-conductive material, with the electrodes formed therein, so as to coat all of the electrodes in a single coating step, without the use of a masking operation.

DESCRIPTION OF THE PREFERRED EMBODIMENTS

Figure 1A:
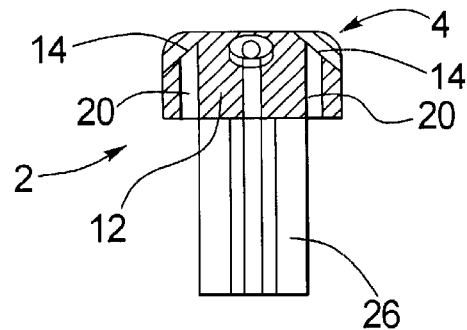
FIGS. 1A and 1B show, respectively in a side view partly in cross-section, and in a top end view, an electrode head before it has been p provided with wire pins intended to form conductive electrode surfaces on an end surface of the electrode head.
Figure 1B:
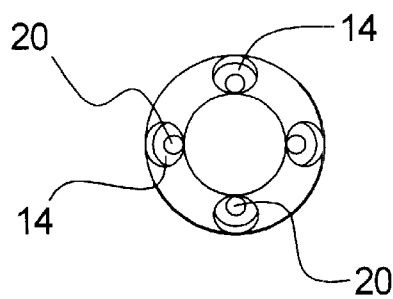
Figure 3:
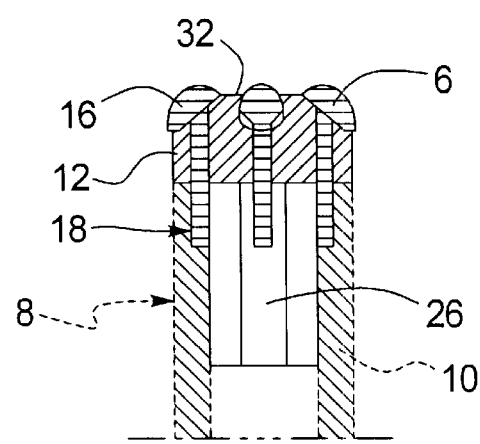
FIG. 3 shows, in a side view similar to FIG. 1A, an electrode head having been coated with a porous material, using the method according to the present invention.

In FIGS. 1A and 1B there is shown a multipolar electrode head 2 which is to be provided, in a tip region 4 thereof, with four round, circumferentially spaced apart conductive electrode surfaces 6 (shown in FIG. 3) constituting contacts which are to have different polarity. As indicated in FIG. 3, the electrode head 2 is adapted to be mounted at a distal end of an electrode cable or pacing lead 8 intended for providing electric heart stimulation by means of a heart stimulation apparatus or pacemaker (not shown). In FIG. 3 the pacing lead 8 is indicated by its external layer of insulation 10.

The electrode head 2 has a tip portion with a ceramic part 12 having on a forward end surfaces thereof, four notches 14 formed as round chamferings. The notches 14 provide seatings for the head portions 16 of four platinum pins 18 (shown in FIG. 3) which are placed in mutually parallel holes 20 (FIG. 1A) extending axially through the ceramic part 12. The pin head portions 16 constitute the spaced apart conductive electrode surfaces 6 on the forward end surface of the ceramic part 12.

Figure 2:
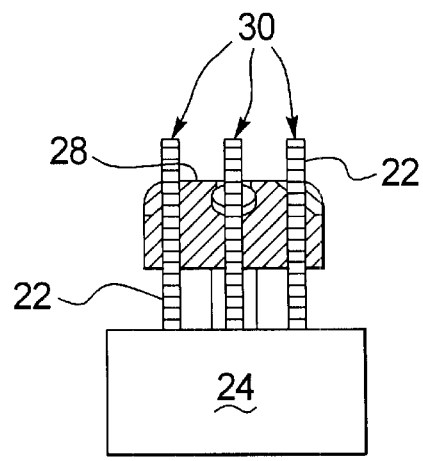
FIG. 2 shows, in a view similar to FIG. 1A, a stage of bringing together an electrode head and wire pins which are intended to form the conductive electrode surfaces of the electrode head.

In order to place the platinum pins 18 in the holes 20, it may be expedient first to place four straight platinum wire sections 22 (FIG. 2) in a ring-shaped fixture 24 having a central opening for the shaft portion 26 or the electrode head 2. The fixture 24 with its four wire sections 22 is then moved upwardly toward the ceramic part 12, so that the wire sections (which are inserted in the holes 20) ar4e brought to project a suitable length above the flat end surface 28 of the ceramic part. After this mutual positioning of the wire sections 22 and ceramic part 12, the free wire lengths above the end surface 28 are melted using a suitable laser beam 30, as schematically indicated in FIG. 2. When the free lengths of the platinum wire sections have been duly melted to form the head portions 16, the electrode head is ready for coating. At this stage, the tip region 4 thereof appears basically as shown in FIG. 3.

Although modifications and changes may be suggested by those skilled in the art, it is the intention of the inventor to embody within the patent warranted heron all changes and modifications as reasonably and properly come within the scope of his contribution to the art.

I claim as my invention:

1. A method for coating a tip region of a multipolar electrode head adapted for mounting at a distal end of a medical stimulation lead, comprising the steps of:

providing an electrode head having a tip with a non-conducting part having a plurality of spaced-apart conductive electrode surfaces; and directly coating an unmasked region of said tip with a tissue compatible material to simultaneously coat all of said conductive electrode surfaces.

2. A method as claimed in claim 1 comprising coating said tip with a tissue compatible material selected from the group consisting of titanium nitride, carbon and platinum black.

3. A method for manufacturing a multipolar electrode head adapted for mounting at a distal end of a medical stimulation lead, comprising the steps of:

providing a non-conducting part with a plurality of recesses therein;

inserting electrically conductive wires respectively in said recesses;

forming a plurality of conductive electrode surfaces respectively at said conductive wires on a surface of said non-conducting part, so that said conductive electrode surfaces are spaced apart from each other on said surface of said non-conducting part; and directly coating at least an unmasked portion of said surface of said non-conducting part with a tissue compatible material to simultaneously coat all of said electrode surfaces.

4. A method as claimed in claim 3 comprising providing a ceramic part as said non-conducting part.

5. A method as claimed in claim 3 comprising selecting said coating material from the group consisting of titanium nitride, carbon and platinum black.

6. A method as claimed in claim 3 wherein the step of forming said conductive electrode surfaces comprises inserting said wires into the respective recesses from a bottom of said non-conducting part so that respective portions of said wires project above said surface of said non-conducting part, and flattening said projecting portions of said respective wires with a laser beam.

7. A method as claimed in claim 3 wherein the step of forming said conductive electrode surfaces comprises providing each of said conductive wires with an enlarged end, and inserting said wires in said respective recesses from above said surface of said non-conducting part so that said enlarged ends are disposed on said surface of said non-conducting part.

* * * * *